United States Patent [19]

Picha

[11] Patent Number: 5,342,628
[45] Date of Patent: Aug. 30, 1994

[54] DRUG DIFFUSION POLYMER SYSTEM AND METHOD

[75] Inventor: George J. Picha, Independence, Ohio

[73] Assignee: Applied Medical Research, Inc., Independence, Ohio

[21] Appl. No.: 595,965

[22] Filed: Oct. 11, 1990

[51] Int. Cl.$^5$ ............................................... A61K 9/20
[52] U.S. Cl. .................................. 424/484; 424/485; 424/486
[58] Field of Search ............... 424/482, 485, 484, 486, 424/464, 468

[56] References Cited

U.S. PATENT DOCUMENTS 4,764,380 8/1988 Urquhart et al. .................... 424/484
4,839,177 6/1989 Colombo et al. .................... 424/482

OTHER PUBLICATIONS

A. R. Gennardo. (1985). Remington's Pharmaceutical Sciences, 17th ed. Mack Pub. pp. 1298, 1601, 1299.

Primary Examiner—Thurman K. Page
Assistant Examiner—Raj Bawa
Attorney, Agent, or Firm—Pearne, Gordon, McCoy & Granger

[57] ABSTRACT

A drug diffusion polymer system for the sustained release of drugs includes a composition comprising a polymeric matrix containing a uniform dispersion of a matrix expander and a drug. The matrix expander and drug are each present in the form of solid particulate. Upon exposure to body fluid or water, the matrix expander swells to cause the ingress of fluid into the polymeric matrix for solubilizing and diffusing the drug. Devices may incorporate such drug diffusion compositions as a coating or as a primary material of construction. Such devices may be formed by molding the compositions at room or elevated temperatures depending on the polymer used.

30 Claims, 2 Drawing Sheets

DRUG DIFFUSION POLYMER SYSTEM AND METHOD

BACKGROUND OF THE INVENTION AND PRIOR ART

The present invention generally relates to drug diffusion polymer systems and more particularly, to compositions and devices incorporating such compositions for sustained release of drugs and to methods of making such compositions and devices.

Compositions and devices for the delivery of a drug to an aqueous body environment during a prolonged period of time are well known in the art. These often comprise an admixture of a physiologically acceptable polymer and a drug. In addition to the drug, other additives may be included in the composition to provide drug release. The release of the drug is typically a function of the composition; the device often having a separate utility even though the drug release may be particularly complimentary thereto. As used herein, an aqueous body environment is a subcutaneous, percutaneous or interior region of an animal or human having a body fluid or water presence sufficient for solubilizing and diffusing a drug.

One type of drug release or diffusion composition comprises an imperforate polymer matrix containing a dissolved drug which is permeable through the polymer matrix by diffusion. Such a diffusion system requires a unique matching of polymer and drug properties.

Another type of composition involves dispensing of the drug from a biodegradable polymeric material as described in U.S. Pat. Nos. 3,887,699 and 4,148,871. The degrading polymer component in such a composition burdens the user's system.

It is also known to dispense drugs from porous polymeric compositions characterized by interconnected cells which contain the solid or liquid drug in depots as disclosed in U.S. Pat. No. 4,702,917. The fluid or water of the body environment dissolves the drug and forms a tortuous diffusion pathway. These compositions usually require the use of a relatively large proportion of drug in order to assure porosity. Also, they tend to have an undesirably high diffusion rate, and devices employing such compositions may become prematurely ineffective and require replacement.

Polymeric compositions containing solid drug depots are also used to provide osmotic bursting compositions as disclosed in U.S. Pat. Nos. 3,923,939 and 4,177,256. The water of the body environment is imbibed osmotically into the depots in a serially inward direction to dissolve the drug within the depots and to generate sufficient pressure therein to burst adjacent polymer layers. This release technique imposes particular physical properties such as tensile and modulus characteristics upon the polymer materials which are useful.

Drug diffusion polymeric systems or compositions may be used to form the device itself, especially when the device has no separate or additional utility other than delivery of the drug to the system. More often, the device has a separate utility and the composition may be applied to the device as a coating or otherwise be associated with the device in order to provide a composition or drug delivery surface of predetermined area which is exposed to the body environment. For example, the use of catheters, percutaneous access devices such as feeding devices and peritoneal dialysis devices is associated with a high risk of infection. This risk may be substantially reduced by incorporating a drug release composition into the device with a sustained release of drug to the device surface and body environment of an antibiotic.

The use of drug release compositions as the primary material of construction in such devices has been substantially hindered, if not impeded, by the adverse effects of manufacturing processes and conditions upon drugs and diffusion additives. Problems encountered include drug degradation and drug and/or additive interference with the polymerizing or curing of the primary constructional polymer by the drug and/or additive.

As used herein, the term "drug" broadly includes physiologically or pharmacologically active substances for producing a localized effect at the administration site or a systemic effect at a site remote from the administration site. Such drugs include inorganic and organic compounds, for example, drugs which act on the central nervous system such as hypnotics and sedatives, psychic energizers, tranquilizers, anticonvulsants, muscle relaxants and anti-parkinson agents, antipyretics and anti-inflammatory agents, local anesthetics, anti-spasmodics and anti-ulcer agents, prostaglandins, antibiotics, hormonal agents, estrogenic steroids, progestational steroids, such as for contraceptive purposes, sympathomimetic drugs, cardiovascular drugs, diuretics, antiparasitic agents, hypoglycemic drugs and ophthalmic drugs. The antibiotics are of particular importance and application herein. Illustrative water-soluble antibiotics include, without limitation, cephalothin, neomycin, ampicillin, tobramycin, kanamycin, tetracycline, lincomycin, nitrofurantoin, bacitracin, and nystatin. The drug should be a solid or convertible to solid form by reaction, such as salt formation and crystallization.

SUMMARY OF THE INVENTION

Applicant has discovered improved drug release or diffusion compositions wherein a polymeric component provides a continuous phase or polymeric matrix containing a homogeneous distribution of drug and matrix expander. The matrix expander is swelled by body fluid or water to enable ingress of the fluid into the composition for diffusing the drug into the body environment. The polymeric component or precursors thereof may be combined with the drug and matrix expander and then shaped using molding techniques which cause the polymeric component to be polymerized or cured.

In accordance with the invention, the matrix expander and drug are substantially uniformly dispersed or distributed in sufficiently close proximity in the polymeric matrix to enable ingress of body fluid along and/or through matrix expander particles for solubilization and diffusion of drug particles during a prolonged period of time at a controlled rate. The matrix expander particles are progressively swollen in a direction extending into the polymeric matrix and drug adjacent to the swelling expander is progressively diffused into the body environment. The diffusion of the drug does not result in the formation of interconnected voids or a porosity which characterized the undesirably high diffusion rates of prior art porous compositions.

The matrix expander may be present in amounts ranging from about 5% to about 45% based on the weight of the composition, and more preferably, from about 10% to about 25%, and most preferably, in a weight percentage of about 20%. The use of lesser amounts of matrix expander is preferred since this better maintains the mechanical integrity of the polymeric component. It is therefore advantageous that the matrix expander may be used in amounts less than those necessary to achieve porosity by dissolution of a filler. For example, filler concentrations in the order of 80% by weight are typical to achieve interconnecting cells by filler dissolution.

The amount of drug required will be in part dependent upon the particular physiological or pharmacological activity intended. The concentration of the drug may range up to about 25% based upon the weight of the composition. In connection with antibiotics, drug concentrations of less than about 10% based on the weight of the composition have been found effective, and more typically, the antibiotic concentration may range from about 1% to about 10%. The use of matrix expanders has been found effective to reduce the amount of drug necessary to achieve desired dosages.

In accordance with the illustrated embodiments, the matrix expander and drug comprise solid particles. The body fluid is imbibed into the polymeric matrix upon swelling of the matrix expander for solubilizing and diffusing the drug into the body environment.

The molecular weight of the expander may be selected to influence the drug diffusion rate. For example, similar hydrophilic polymeric expanders of comparatively higher and lower molecular weights respectively provide higher and lower drug diffusion rates throughout sustained time periods.

The rate of drug diffusion may also be influenced by the use of a thin outer resistance membrane or layer which may be the same as or different from that used to form the polymeric matrix. The resistance layer may contain a reduced amount of matrix expander as compared to the polymeric matrix or it may contain no matrix expander. In the latter case, the resistance layer is sufficiently thin to be semipermeable and to permit the passage of body fluid and dissolved drug.

In accordance with the present invention, the compositions may be prepared using vacuum and/or inert atmosphere techniques to prepare and shape the compositions to substantially reduce, if not eliminate, drug oxidation which may reduce drug efficacy or bioactivity. Thus, the compositions may be prepared with the use of an inert atmosphere such as argon or nitrogen. An inert atmosphere may be used during only the final cure of the composition. These techniques are particularly effective for antibiotics.

The use of an inert atmosphere tends to enable composition processing temperatures and times which correspond with temperatures and exposure times heretofore found to degrade the drug. In turn, this enables a wider range of elevated temperature molding techniques to be used to shape or coat the compositions. As used herein, elevated temperature molding techniques contemplate dip molding, blow molding, injection molding, compression molding and coating. Room temperature molding techniques may also be used.

DETAILED DESCRIPTION OF THE INVENTION

Figure 1:
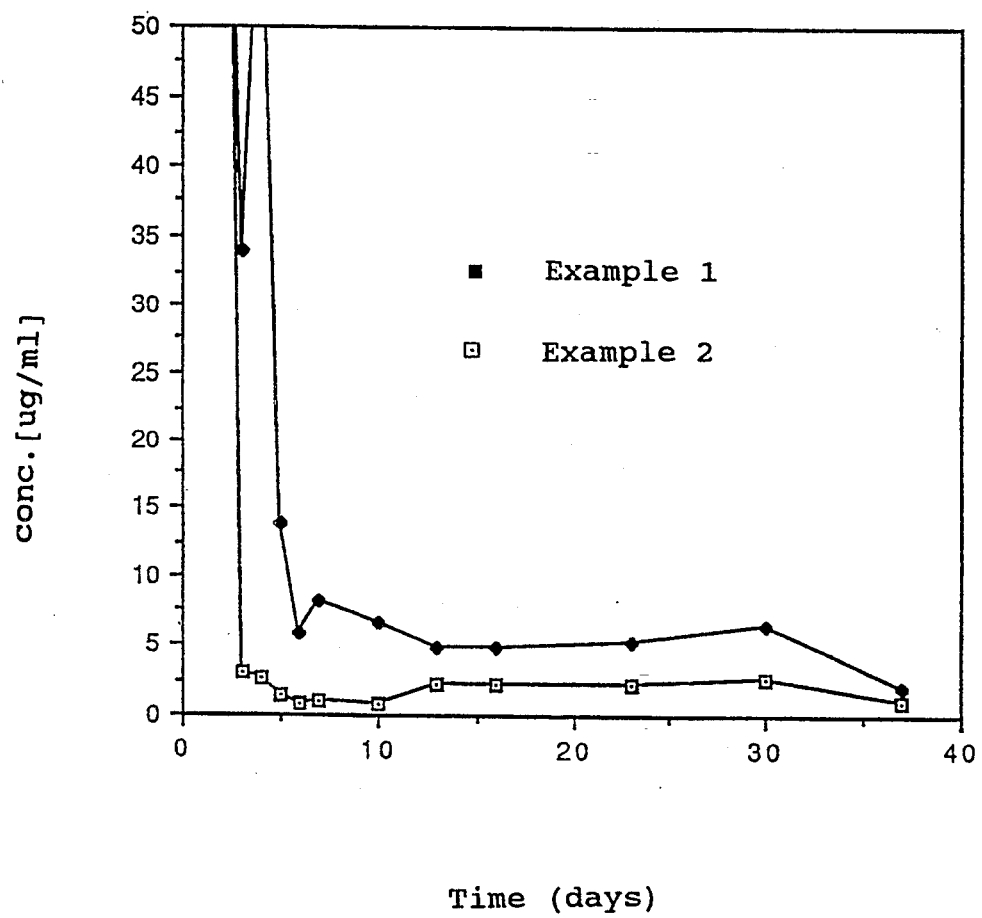
FIG. 1 is a graph showing the relationship of drug diffusion with time for a drug diffusion composition including a polymeric matrix and a matrix expander for diffusing a drug in accordance with the present invention.

In accordance with the invention, the polymeric matrix may be formed of any physiologically acceptable polymer which is sufficiently liquid impermeable and hydrophobic to assure that diffusion control is substantially regulated by the matrix expander coaction with the body fluid. More particularly, it is believed that the matrix expander is swelled by the body fluid and expands the polymeric matrix to cause the ingress of fluid through the polymer matrix resulting from the swelling of the matrix expander particle itself. As used herein, the term polymer also includes homopolymers, copolymers, terpolymers, interpolymers and blends thereof. Illustrative polymers include silicones, polystyrenes, polyurethanes, silicone and polystyrene copolymers, polystyrene and butadiene copolymers, and acrylonitrile-butadiene-styrene resins. Representative silicone polymers include medical grade silicone rubbers such as those suitable for implants: diphenylpolysiloxane, dimethylpolysiloxane (dimethicone), phenylmethylpolysiloxane, trifluoropropylmethylsiloxane, copolymers of dimethylpolysiloxane and polymethylmethacrylate and mixtures thereof.

The matrix expander may comprise a physiologically acceptable hydrophilic polymer or block copolymer including a hydrophilic block which swells to a sufficient degree upon contact with body fluid to cause ingress of body fluid into the drug diffusion composition for solubilization and/or diffusion of the drug to the environment. The polymer should be substantially insoluble in the body fluid in that no significant dissolution should occur within the expected period of exposure to body fluid so as to materially affect the rate of drug diffusion. Further, the solubilization and/or diffusion of the drug should not result in a gross fluid path. In this manner, the diffusion rate is substantially controlled by the amount of matrix expander present and its coaction with the body fluid.

Illustrative examples of matrix expander polymers include hydroxyethyl starch (HES), polyvinylpyrrolidone (PVP) polyacrylic acid, hydroxyethylmethacrylate, polyvinyl alcohol and polyethylene oxide of sufficient molecular weight to provide the desired insolubility in body fluid. Particularly preferred expander include HES and PVP.

In addition to ensuring insolubility, the molecular weight of the expander may also affect the drug diffusion rate. For example, high molecular weight (400,000 to 550,000) HES enables drug diffusion from a silicone matrix at a relatively higher rate than that provided by a similar amount of low molecular weight (150,000 to 350,000) HES from a similar silicone matrix. In each case, enhanced release at effective drug diffusion rates is achieved over a prolonged period of time in the order of about five weeks. In a control system not including matrix expander, drug diffusion effectively stops after six to seven days.

The matrix expander polymer should not interfere with the polymerization and/or curing of the polymer which forms the polymeric matrix. The curing may also be influenced by the molecular weight of the expander. For example, PVP having a molecular weight of about 10,000 tended to interfere with the cure of a silicone polymeric matrix. However, no adverse cure effects were observed when PVP having a molecular weight of 360,000 was used with the silicone polymeric matrix.

The matrix expander should be able to withstand temperatures encountered in the molding of the polymeric matrix e.g. 100° C. HES and PVP have been found to display these further desirable properties and may therefore be used in the injection molding and compression molding processes used to form the drug diffusion device. For example, compositions comprising polymeric matrices of silicone with HES or PVP matrix expanders and antibiotics may be used to directly manufacture of coat devices such as catheters, tubing, endotracheal tubing, urologic devices, percutaneous feeding devices or other medical products using molding techniques which include polymerizing or curing the silicone polymers.

The sizes of the solid particles of the matrix expander and the drug are not critical. However, the matrix expander particles should preferably be of a size sufficient upon swelling to expand the polymeric matrix and cause the ingress of fluid. Satisfactory results have been obtained with particles in the range of from about several microns to about several hundreds of microns in diameter.

In the following Examples 1 and 2, compositions in accordance with the present invention are prepared using a silicone rubber for the continuous polymeric matrix phase, HES as the matrix expander and tobramycin antibiotic as a drug. As described more fully below, a compression molding technique is used to concurrently shape and polymerize/cure the silicone containing the HES and tobramycin into disc shape specimens suitable for diffusion testing.

The particular silicone rubber is a medical grade polymer sold by the Dow Corning Company under the designation silastic Q7-4840. This is a two part system with an addition type cure causing a rubbery elastomer to form. The cure time decreases with increasing temperature and a substantially instantaneous cure is obtained by raising the polymer temperature to 100° C.

The matrix expander is a hydroxyethyl starch sold by Kendall McGaw Laboratories, Inc., California, USA and Ajinomoto, Japan. It is prepared from corn starch with an average degree of substitution of 0.7-0.8. The molecular weight is indicated to be 400,000 to 550,000.

The tobramycin is an antibiotic available as a powder from Eli Lilly and Co., Indiana, USA. It is active against Staphylococci including *S. aureus* and *S. epidermidis*.

The silicone polymer A and B parts are mixed together in the recommended proportions at room temperature. The HES and tobramycin are added as solids to the mixed silicone and a fluorocarbon solvent is added to enhance mixing and assure a homogeneous dispersion of HES and tobramycin throughout the silicone. The fluorocarbon is non-reactive, and does not interfere with polymer curing. It is subsequently removed by evaporation after completion of the mixing procedure. To that end, the mixture is placed under vacuum for ten minutes and then further mixed. This two step procedure is repeated several times until no further fluorocarbon gas evolution is observed during the vacuum step.

In the final fluorocarbon gas removal cycle, the composition mixture is purged of oxygen by substitution of a nitrogen atmosphere. The nitrogen atmosphere is subsequently evacuated. This procedure reduces the possibility of oxidation of the HES and tobramycin during thermal processing of the composition. In addition, the polymer constituent of the composition may be polymerized and/or cured in an inert atmosphere to further reduce the risk of oxidation of the HES and tobramycin. As discussed below more fully, the latter is believed to suppress bioactivity.

The composition mixture is compression molded at 100° C. for ten minutes to yield a cured silicone polymeric matrix containing a homogeneous dispersion of the solid HES and tobramycin. For diffusion testing, disc shaped samples having a diameter of 1.0 cm and a thickness of 0.1 cm were molded. The weight proportions of the constituents of the compositions are set forth in Table I below.

TABLE I

|  | Example 1 | Example 2 |
|---|---|---|
| Silicone | 75 | 78 |
| HES | 20 | 20 |
| Tobramycin | 5 | 2 |

The in vitro drug release rate was evaluated on sample discs in accordance with Examples 1 and 2 by measuring the amount of drug diffused into fresh saline solutions on a daily basis. Thus, a sample was placed in a 2 ml saline solution, incubated at 37° C. for 24 hours and the concentration of drug in the saline solution was measured. The sample was then placed in a fresh saline solution and the procedure was repeated. Ten samples of compositions in accordance with each of Examples 1 and 2 were simultaneously tested and the results were averaged. The amount of tobramycin in the saline solution was determined spectrophotometrically using Emit Tobramycin Assay (Syva). The results are graphically reported in FIG. 1.

As shown in FIG. 1, there is a two phase time-drug release pattern. Phase I is characterized by high daily release and a rapid decrease in daily release after 100 hours. Phase I usually lasts about 4 or 5 days. The initial high drug concentration release is associated with the leaching of drug on or at the surface of the sample. Phase II is characterized by a much lower daily release and a substantially decreased slope.

The absolute amount of drug released or diffused is porportional to the concentration of drug in the composition. Thus, it is believed that the drug release is substantially controlled by the matrix expander.

In order to stabilize the daily release rate and limit the high release rate during Phase I, a resistance or resistive membrane may be applied to the surface of the polymeric matrix. The resistance membrane may also be formed of silicone elastomer or other polymeric compositions. In this instance, a room temperature vulcanizing silicone may be used in the form of a silicone rubber dispersion. The disc may be dip coated in the dispersion and air dried at room temperature. The thickness of the membrane may be controlled by adjusting the concentration of silicone polymer in the dispersion or through multiple coatings. Due to its relative thinness, the resistance membrane is substantially semipermeable to the body fluid and dissolved drug. The permeability of fluid and dissolved drug through the membrane may be further controlled by the addition of a matrix expander to the silicone dispersion.

Figure 2:
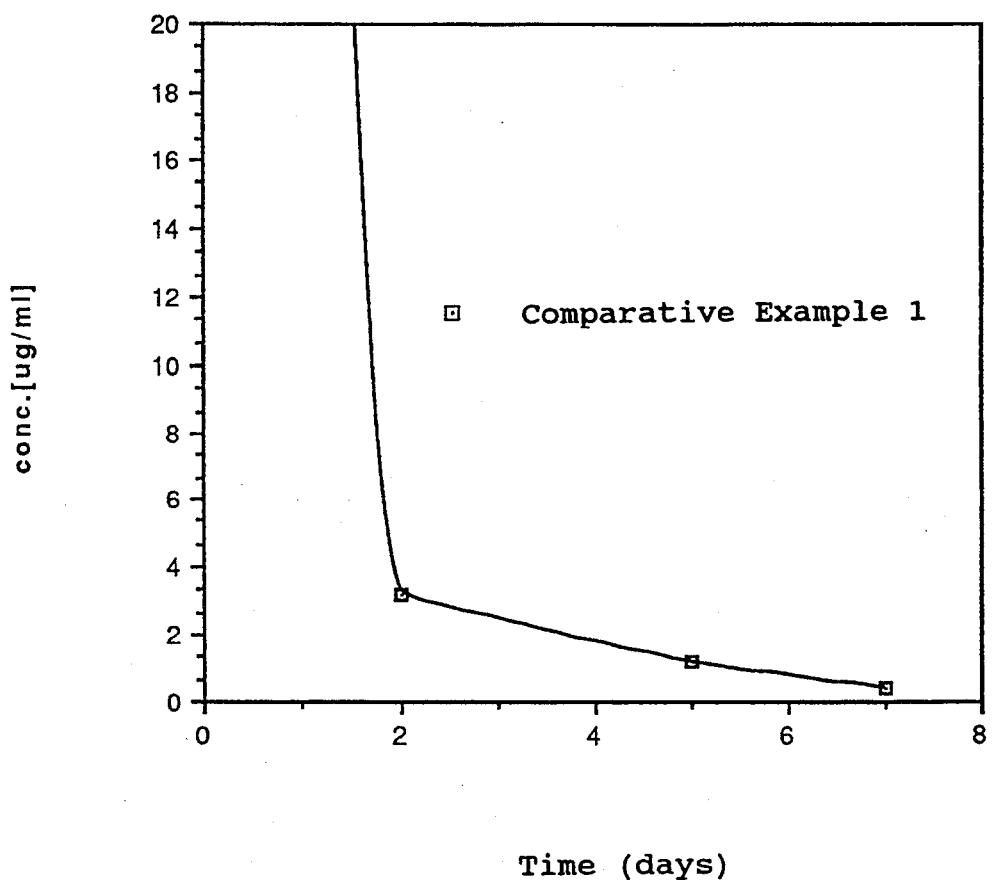
FIG. 2 is a graph similar to that of FIG. 1 showing the relationship of drug diffusion with time for a similar composition without the use of a matrix expander.

Comparative Example 1 was prepared in the same manner as described above using 5% tobramycin and no matrix expander. The composition of Comparative Example 1 was tested as described above to characterize its release rate and the results are shown in FIG. 2. In this case, Phase I lasts for about 50 hours or two days.

Thereafter, Phase II lasts about 125 hours or five days. The release rate approaches zero after about 7 days and there is no further effective drug release.

In illustration of the maintenance of bioactivity in accordance with the present invention, antibiogram type tests were used to compare the efficacy of tobramycin contained in compositions prepared in accordance with the invention with and without the use of an inert nitrogen atmosphere to prevent drug degradation. The procedure and composition of Example 1 were repeated with the use of a nitrogen atmosphere during the final fluorocarbon gas removal cycle and the compression molding of the composition to form the disc shaped samples of Example 3 having a diameter of 1.0 cm and a thickness of 0.1 cm. The disc shaped samples of Example 4 were similarly prepared with the omission of the nitrogen atmosphere in the processing.

The discs of Examples 3 and 4 were tested against *E. Coli* bacteria. To that end, the bacteria was uniformly cultured on agar test plates and discs were placed on top of the plates. Ten discs in accordance with each of Example 3 and Example 4 were prepared in this manner. The test plates and discs were incubated for 24 hours at 37° C. and high humidity.

Following the incubation period, a zone of inhibition of bacterial growth was determined by measurement of the diameter of the area of non-bacteria growth on the surface of the agar. The average diameter of the zones of inhibition for Examples 3 and 4 were respectively 24 mm and 17 mm.

Accordingly, the use of an inert atmosphere to limit oxidation of the drug tends to avoid and/or lessen any reduction in the bioactivity of the drug due to high temperature processing.

As indicated, the inert atmosphere processing in accordance with the invention enables improved drug potency as compared with air processing. IT has also been observed that the processing temperatures and/or exposure times to elevated temperatures are also increased. For example, tobramycin degrades and exhibits a reduced drug potency upon molding in an air environment at temperatures of about 100° C. However, the use of an inert atmosphere in accordance with the invention enables elevated temperature molding of compositions containing tobramycin at temperatures in the range of about 115° to 120° C.

It should be evident that this disclosure is by way of example and that various changes may be made by adding, modifying or eliminating details without departing from the fair scope of the teaching contained in this disclosure. The invention is therefore not limited to particular details of this disclosure except to the extent that the following claims are necessarily so limited.

We claim:

1. A composition for administering a drug continuously to an aqueous body environment during a prolonged period of time at a controlled rate comprising a solid drug and a matrix expander substantially homogeneously dispersed in a polymeric matrix, said matrix expander being substantially insoluble in water but sufficiently water swellable to cause the ingress of water within the polymer matrix for dissolving and diffusing said drug into said aqueous body environment, said polymeric matrix comprising a polymerized or cured continuous phase which is sufficiently liquid impermeable and hydrophobic to assure that drug release is substantially regulated by said matrix expander swelling, said matrix expander being sufficiently water insoluble to provide drug diffusion without dissolution of said matrix expander sufficient to materially affect the rate of drug diffusion, and said drug diffusion along and/or through said matrix expander and into said body environment without forming interconnected voids or porosity in said polymeric matrix.

2. The composition of claim 1, wherein said matrix expander comprises a physiologically acceptable hydrophilic polymer.

3. The composition of claim 2, wherein said matrix expander is selected from the group consisting of polyvinylpyrrolidone and hydroxyethyl starch.

4. The composition of claim 3, wherein said polymeric matrix is formed of a material selected from the group consisting of silicone and polyurethane.

5. The composition of claim 4, wherein said drug is an antibiotic.

6. The composition of claim 5, wherein said composition comprises from about 5% to about 45% of said matrix expander based on the weight of said composition and the remainder comprises said drug.

7. The composition of claim 6, wherein said composition comprises from about 10% to about 25% of said matrix expander based on the weight of said composition and the remainder comprises said drug.

8. The composition of claim 5, wherein said composition comprises about 25% or less of said drug.

9. The composition of claim 8, wherein said composition is moldable at temperatures of up to 115° C.

10. A method of making a device for the release of a drug to an aqueous body environment during a prolonged period of time at a controlled rate comprising selecting a polymeric matrix material which is substantially impermeable to water in the aqueous body environment, selecting a matrix expander which is substantially insoluble in water but sufficiently water swellable to cause the ingress of water within the matrix material upon exposure to the water of said aqueous body environment, providing the drug as a solid at room temperature and at the use temperature for dissolution by the water of the aqueous body environment, uniformly dispersing the drug and matrix expander in the polymeric material to form a homogeneous blend, molding and curing said homogeneous blend at an elevated temperature to form a device of the desired shape and construction, said polymeric material providing in said device a polymerized or cured continuous phase which is sufficiently liquid impermeable and hydrophobic to assure that drug release is substantially regulated by said matrix expander swelling, said matrix expander being sufficiently water insoluble to provide drug diffusion without dissolution of said matrix expander sufficient to materially affect the rate of drug diffusion, and said drug diffusing along and/or through said matrix expander and into said body environment without forming interconnected voids or porosity in said polymeric matrix.

11. The method of claim 10, wherein the step of molding and curing said homogeneous blend are performed in an inert atmosphere.

12. The method of claim 11, wherein the step of molding and curing said homogeneous blend is performed at a temperature greater than that resulting in drug oxidation in an air environment.

13. The method of claim 11, wherein the drug has a oxidation temperature and the step of molding and curing said homogeneous composition is performed at a temperature greater than said drug oxidation temperature.

14. The method of claim 10, wherein the step of dispersing the drug and matrix expander in the polymeric matrix material includes purging the mixture of oxygen by substitution of an inert atmosphere.

15. The method of claim 10, wherein the step of molding and curing said homogeneous blend is performed in an inert atmosphere.

16. The method of claim 10, wherein the step of molding and curing said homogeneous blend includes the use of an elevated temperature molding process selected from the group consisting of dip molding, blow molding, injection molding, compression molding and casting.

17. A method of releasing a drug to an aqueous body environment during a prolonged period of time at a controlled rate comprising providing a polymeric matrix containing a homogeneous dispersion of the drug and a matrix expander, exposing said polymeric matrix to the body environment to swell said polymeric matrix and cause water to be imbibed into the matrix for contact with the drug, and solubilizing drug contacted by the imbibed water for diffusion into the aqueous body environment, said polymeric matrix comprising a polymerized or cured continuous phase which is sufficiently liquid impermeable and hydrophobic to assure that drug release is substantially regulated by said matrix expander swelling, said matrix expander being sufficiently water insoluble to provide drug diffusion without dissolution of said matrix expander sufficient to materially affect the rate of drug diffusion, and said drug diffusing along and/or through said matrix expander and into said body environment without forming interconnected voids or porosity in said polymeric matrix.

18. The method of claim 17, wherein said dispersion of matrix expander is progressively swollen in a direction extending into said polymeric matrix.

19. The method of claim 18, wherein said polymeric matrix and matrix expander are substantially insoluble in the water of the aqueous body environment, and said drug is substantially insoluble in said polymeric matrix.

20. The method of claim 19, wherein said polymeric matrix is sized and shaped so that said drug diffuses into said aqueous body environment for a continuous period of time equal to about at least two weeks.

21. A drug diffusion device for administering a drug continuously to an aqueous body environment during a prolonged period of time comprising a composition including a solid drug and a matrix expander substantially homogeneously dispersed in a polymeric matrix, said polymeric matrix being substantially impermeable to water, and said drug being soluble in water, said matrix expander being substantially insoluble in water but sufficiently water swellable to cause the ingress of water within the polymer matrix for dissolving and diffusing said drug into said aqueous body environment, said polymeric material providing in said device a polymerized or cured continuous phase which is sufficiently liquid impermeable and hydrophobic to assure that drug release is substantially regulated by said matrix expander swelling, said matrix expander being sufficiently water insoluble to provide drug diffusion without dissolution of said matrix expander sufficient to materially affect the rate of drug diffusion, and said drug diffusing along and/or through said matrix expander and into said body environment without forming interconnected voids or porosity in said polymeric matrix.

22. A device as set forth in claim 21, wherein said matrix expander comprises a physiologically acceptable hydrophilic polymer.

23. A device as set forth in claim 22, wherein said matrix expander is selected from the group consisting of polyvinylpyrrolidone and hydroxyethyl starch.

24. A device as set forth in claim 23, wherein said polymeric matrix is formed of a material selected from the group consisting of silicone and polyurethane.

25. A device as set forth in claim 24, wherein said composition is the primary construction material used to form said device.

26. A device as set forth in claim 24, wherein said composition is a coating applied to said device.

27. A device as set forth in claim 26, wherein said device is a catheter and said polymeric matrix is formed of silicone, said matrix expander is hydroxyethyl starch and said drug is an antibiotic.

28. A device as set forth in claim 21, wherein said device includes a drug diffusion surface adapted to be exposed to said body environment for diffusion of drug into the body environment, said drug diffusion surface including a resistance membrane for limiting initial drug diffusion rates.

29. A device as set forth in claim 28, wherein said resistance membrane comprises a thin layer of a physiologically acceptable polymer.

30. A device as set forth in claim 29, wherein said thin layer of polymer has matrix expander homogeneously dispersed therein.

* * * * *